US00PP32531P2

(12) United States Plant Patent
Austin

(10) Patent No.: US PP32,531 P2
(45) Date of Patent: Dec. 1, 2020

(54) ***ROSA HYBRIDA* PLANT NAMED 'AUSWAGSY'**

(50) Latin Name: *Rosa hybrida*
Varietal Denomination: AUSwagsy

(71) Applicant: David Austin Roses Ltd., Albrighton, Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 16/602,855

(22) Filed: Dec. 12, 2019

(51) Int. Cl.
*A01H 5/02* (2018.01)
*A01H 6/74* (2018.01)

(52) U.S. Cl.
USPC ..... Plt./103
CPC ..... *A01H 6/749* (2018.05)

(58) Field of Classification Search
USPC ..... Plt./103
CPC ..... A01H 6/749; A01H 5/02
See application file for complete search history.

*Primary Examiner* — Keith O. Robinson
(74) *Attorney, Agent, or Firm* — KPPB LLP

(57) ABSTRACT

A variety of rose plant of the shrub class, named 'AUSwagsy'. The 'AUSwagsy' is a variety of a rose shrub that produces a cut-flower rose having ivory colored, double blooms with many petals arranged in an informal formation with good vase life and a fresh fragrance.

1 Drawing Sheet

Classification: The present invention relates to a new *Rosa hybrida* shrub of the market class 'English Rose'.

Variety denomination: The new plant has the varietal denomination 'AUSwagsy'.

CROSS-REFERENCE TO RELATED APPLICATION

The present application claims priority to European Plant Variety Right 2019/2594, filed Oct. 11, 2019.

ORIGIN OF INVENTION

This invention relates to a new and distinct variety of shrub rose plant named 'AUSwagsy', which was originated from the cross-pollination of the two 'unnamed' and unpatented seedlings of *Rosa hybrida.*

BACKGROUND OF THE INVENTION

The primary objective of this breeding was to produce a cut-flower rose variety having ivory colored, double blooms with many petals arranged in an informal formation with good vase life and a fresh fragrance.

SUMMARY OF THE INVENTION

Among the features which distinguish the new variety from others presently available and commercial rose cultivars known to the inventor is the following combination of characteristics: ivory colored flowers with many petalled, double blooms, and strong stems.

Asexual reproduction of the new variety by budding as performed in Albrighton, Britain shows that the foregoing and other distinguishing characteristics come true to form and are established and transmitted through succeeding asexual propagations. 'AUSwagsy' may be asexually propagated by budding. The budding successfully occurred on an unpatented plant/rootstock *Rosa lnermis* for the observed plants.

COMPARISON WITH PARENTS

The maternal and paternal parents of 'AUSwagsy' are two unnamed seedlings. The new rose may be distinguished from its seed parent, by the following combination of characteristics: the seed parent has a flower which is pink in color and hybrid tea in form with no fragrance compared to the ivory colored flowers with medium fragrance of 'AUSwagsy'. The new rose may be distinguished from its pollen parent, by the following combination of characteristics: the pollen parent also has a pink flower, which is smaller in size when compared to 'AUSwagsy'.

COMPARISON WITH THE CLOSEST COMMERCIALLY AVAILABLE CULTIVAR

The closest commercially available cultivar to the new variety is 'AUSoblige', U.S. Plant Pat. No. 29,874. The bloom size of 'AUSoblige' is 11 cm in diameter, very large, and so bigger than the bloom size of 'AUSwagsy', which is 9.5 cm. The blooms of 'AUSwagsy' have more petals, 105 per bloom, as opposed to 60 per bloom for 'AUSoblige'. Both varieties are a shade of white/cream/ivory however 'AUSoblige' does exhibit a touch of very pale pink color in the center.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSwagsy' specimens were made at a nursery in Albrighton, Wolverhampton, United Kingdom. The following description is of 5 year-old rose plants of the new variety grown in a greenhouse environment in Albrighton, Britain in the month of June. Phenotypic expression may vary with environmental, cultural and climatic conditions, as well as differences in conditions of light and soil.

FLOWER CHARACTERISTICS

Blooming habit: Continuous. The number of blooms per plant during the growing season is profuse, but there are too many to count.

Bud:

*Size*.—About 2.8 cm long and 2.5 cm in diameter when the petals start to unfurl.

*Form*.—The bud form is blunt topped.

*Color*.—When sepals first divide, the bud color is RHS 154B (yellow-green group). When half blown, the upper sides of the petals are RHS 2D (yellow group), and the lower sides of the petals RHS 2D (yellow group).

*Calyx*.—Shape: star shape, with the sepals folding back against the stems. Length: 8.5 cm. Diameter: 8.5 cm.

*Sepals*.—Arrangement: Regularly arranged. Color: Upper Surface: RHS 146B (yellow-green group) with RHS 186A (grayed-purple group) in the center. Lower Surface: RHS 144A yellow-(green group) with RHS 185B (grayed-purple group) in the center. Length: 4.1 cm. Width: 1.1 cm. Shape: Lanceolate. Surface texture: Upper Surface: Smooth-slightly hairy. Lower Surface: Slightly coarse. Number: There are 3 lightly appendaged sepals, and 2 unappendaged sepals with smooth edges. Sepal Extensions: Weak.

*Receptacles*.—Color: RHS 144A (yellow-green group). Shape: Funnel. Size: Slender, about 1.5 cm long×0.8 cm wide. Surface: Smooth.

*Peduncle*.—Length: Medium, averaging about 9.1 cm. Surface: Smooth. Color: RHS 144A (yellow-green group). Strength: Strong.

Blooms:

*Size*.—Large, average open diameter is about 9.5 cm.

*Borne*.—Singly having a rounded shape.

*Stems*.—Strength: Strong, average length is about 100 cm. Diameter: 7 mm.

*Form*.—When first open, bloom is flat. Permanence of bloom: flattens.

*Flower type*.—Double.

Petalage: Number of petals under normal conditions: 105.

*Color*.—The upper sides of the petals are RHS 155A (white group). The reverse sides of the petals are RHS 155A (white group). The base of the petals has a yellow shade basal spot RHS 5C (yellow group) on both inner and outer side.

*Variegations*.—None.

*Discoloration*.—The general tonality at the end of the first day is RHS 2D (yellow group), and at the end of the third day is RHS 155A (white group).

*Fragrance*.—Slight. Character of fragrance: Citrus and cucumber.

Petals:

*Texture*.—Smooth and velvety.

*Size*.—Width: 4.4 cm.

*Length*.—5.3 cm.

*Surface*.—Smooth.

*Shape*.—Oval.

*Margin*.—Entire. No notches/undulations present. Very little reflexing present or incisions.

*Apex shape*.—Rounded.

*Base shape*.—Acute.

*Form*.—Incurved.

*Arrangement*.—Informal.

*Petaloids*.—Number: None.

*Persistence*.—Petals hang on and dry.

*Lastingness*.—On the plant: not tested. As a cut flower: about 12 days.

Reproductive parts:

*Stamens*.—Number: approximately 60. Length: 7-8 mm.

*Anthers*.—Length: 1 mm. Color: RHS 13C (yellow group). Arrangement: Regular around styles.

*Filaments*.—Color: RHS 3C (yellow group). Length: 5-6 mm.

*Pollen*.—Color: RHS 17B (yellow-orange group). Amount: Scarce.

*Pistils*.—Number: 45. Length: 8 mm.

*Styles*.—Color: Mostly RHS 155A (white group). Length: 7 mm.

*Stigmas*.—Color: RHS N66C (red-purple group) with RHS 10C (yellow group). Length: 1 mm.

*Hips*.—NONE Observed.

PLANT CHARACTERISTICS

Plant form: Shrub.

Plant growth: Vigorous.

Age to maturity: 2 years.

Mature plant: Height: 90 cm. Width: 65 cm.

Rootstock: *Rosa lnermis* for the observed plants.

Foliage:

*Number*.—Leaflets on normal mid-stem leaves is: 5 or 7 (including terminal leaflet).

*Size*.—Large, about 20 cm long×15 cm wide.

*Quantity*.—Normal. Number of leaves per flowering stem is: approx. 6-8.

*Color*.—New foliage: Upper side: RHS 187B (grayed-purple group) with RHS 147B (yellow-green group). Lower side: 183A (grayed-purple group). Old foliage: Upper side: RHS 139A (green group). Lower side: RHS 138A (green group).

Leaflets:

*Size*.—About 8.5 cm long×5 cm wide.

*Shape*.—Pointed oval.

*Base shape*.—Cordate.

*Apex shape*.—Acute.

*Texture*.—Leathery.

*Glossiness*.—Strong.

*Edge*.—Serrated.

*Serrations*.—Small.

*Petiole*.—Color: RHS 144B (yellow-green group). Length: 4.5 cm. Width: 2 mm. Surface Texture: Glandular with prickles on reverse.

*Petiole rachis*.—Color: RHS 144B (yellow-green group). Underside: with prickles.

*Stipules*.—Length: 1.5 cm, glandular. Color: RHS 143B (green group).

*Auricle*.—Shape: Lanceolate. Length: 2 cm. Width: 1 mm. Color: RHS 143B (green group).

*Vein color*.—RHS 139A (green group).

*Venation pattern*.—Reticulate.

Wood:

*New wood*.—Color: RHS 147B (green group) with streaks of RHS 185B (grayed-purple group). Bark: Smooth.

*Old wood*.—Color: RHS 147B (yellow-green group). Bark: Smooth.

Branching habit:

*Number*.—N/A.

*Dimensions*.—N/A.

Stems:

*Mature stem*.—Length: 100 cm. Diameter: 7 mm.

*Internode distance*.—17 cm. The above measurements are all variable, depending on growing conditions in a season.

*Stem pubescence present*.—No.

Prickles:

*Quantity*.—On main canes from base: All prickles are very small — less than 4 mm. Number per stem length: 1-2 per 20 cm.

*Form*.—Concave curved inward.

*Length*.—4 mm.

*Color when young*.—RHS 60A (red-purple group).

*Color when mature*.—RHS 174A (grayed-orange group).

Small prickles:

*Quantity*.—Main stalk: Few. Number per stem length 1-2 per 20 cm.

*Color*.—When young: RHS 60A (red-purple group). When mature: RHS 174A (grayed-orange group).

Disease resistance:

*Powdery mildew* (*podosphaera pannosa*).—Resistant.

*Downy mildew* (*peronospora species*).—Resistant.

*Blackspot* (*diplocarpon rosae*).—N/A — not prevalent in greenhouse conditions.

*Rust* (*phragmidium tuberculatum*).—N/A — not prevalent in greenhouse conditions.

Pest resistance: Not tested.

Winter hardiness: Not tested.

Growing conditions: Normal greenhouse conditions.

What is claimed is:

1. A new and distinct variety of rose plant of the shrub class, substantially as herein shown and described.

* * * * *

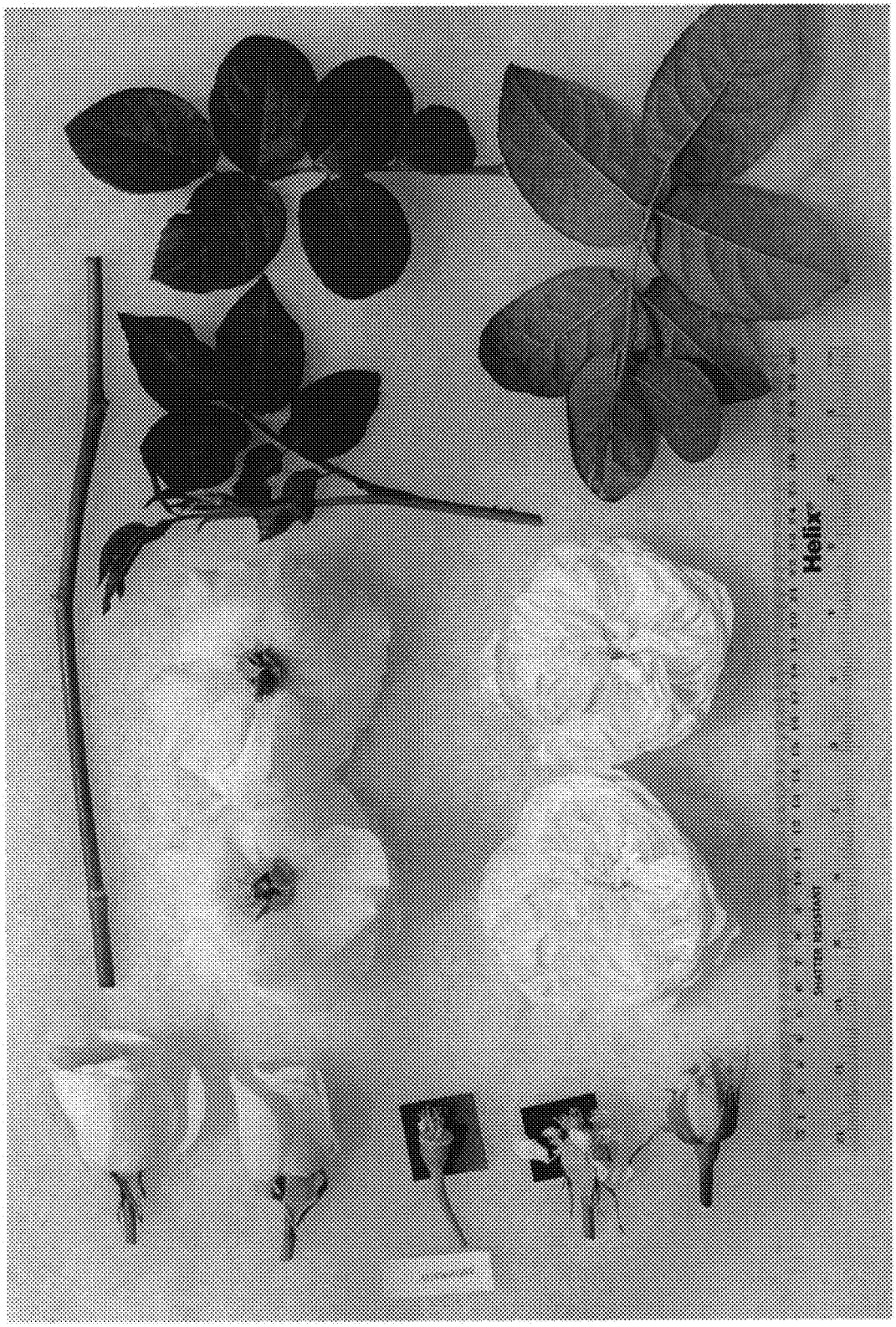
Helix